United States Patent
Jackson

(10) Patent No.: US 7,881,786 B2
(45) Date of Patent: Feb. 1, 2011

(54) SUPPRESSION OF HIGH RATE PACING FOR REDUCING MYOCARDIAL ISCHEMIC IRRITABILITY

(75) Inventor: Troy E. Jackson, New Brighton, MN (US)

(73) Assignee: Medtronic, Inc., Minneapolis, MN (US)

( * ) Notice: Subject to any disclaimer, the term of this patent is extended or adjusted under 35 U.S.C. 154(b) by 382 days.

(21) Appl. No.: 11/118,689

(22) Filed: Apr. 29, 2005

(65) Prior Publication Data

US 2006/0247700 A1   Nov. 2, 2006

(51) Int. Cl.
*A61N 1/362* (2006.01)
(52) U.S. Cl. ............................. 607/9; 607/20
(58) Field of Classification Search ............ 607/9, 607/14
See application file for complete search history.

(56) References Cited

U.S. PATENT DOCUMENTS

| | | | |
|---|---|---|---|
| 4,428,378 A * | 1/1984 | Anderson et al. ............. 607/19 |
| 4,554,920 A * | 11/1985 | Baker et al. ................... 607/17 |
| 4,941,471 A | 7/1990 | Mehra .................. 128/419 PG |
| 4,944,298 A | 7/1990 | Sholder |
| 5,117,824 A | 6/1992 | Keimel et al. ........... 128/419 D |
| 5,282,465 A | 2/1994 | VanDerVeen et al. |
| 5,383,910 A * | 1/1995 | den Dulk ...................... 607/14 |
| 5,431,689 A * | 7/1995 | Weinberg et al. ............. 607/14 |
| 5,609,612 A * | 3/1997 | Plicchi et al. ................. 607/17 |
| 5,713,929 A | 2/1998 | Hess et al. ..................... 607/14 |
| 5,792,193 A | 8/1998 | Stoop |
| 5,814,085 A | 9/1998 | Hill .............................. 607/14 |
| 5,882,352 A * | 3/1999 | Duncan et al. .................. 607/4 |
| 5,944,743 A | 8/1999 | Janssens ......................... 607/9 |
| 5,978,709 A | 11/1999 | Begemann et al. ............ 607/14 |
| 6,115,630 A * | 9/2000 | Stadler et al. ................ 600/521 |
| 6,128,526 A | 10/2000 | Stadler et al. ................ 600/517 |
| 6,185,459 B1 | 2/2001 | Mehra et al. .................. 607/14 |
| 6,216,035 B1 | 4/2001 | Stahl et al. |
| RE37,480 E | 12/2001 | Denker ......................... 607/14 |
| 6,370,431 B1 * | 4/2002 | Stoop et al. .................... 607/14 |
| 6,442,429 B1 | 8/2002 | Hill et al. ....................... 607/14 |
| 2001/0007948 A1 * | 7/2001 | Stoop et al. .................... 607/14 |
| 2003/0191403 A1 | 10/2003 | Zhou et al. ................... 600/515 |
| 2003/0233130 A1 | 12/2003 | Padmanabhan et al. ........ 607/9 |

* cited by examiner

*Primary Examiner*—Carl H. Layno
*Assistant Examiner*—Jon-Eric Morales
(74) *Attorney, Agent, or Firm*—Michael J. Ostrom; Stephen W. Bauer

(57) ABSTRACT

A medical device capable of delivering automatic rate-adjusting pacing therapies is provided having an adjustable upper rate limit responsive to an indication of myocardial irritability. The device, which may be embodied as a pacemaker, a pacemaker/cardioverter/defibrillator, or the like, responds to the detection of an arrhythmia as an indicator of myocardial irritability by adjusting an upper rate limit. The adjusted upper rate limit is applied as the maximum allowable pacing rate during delivery of any pacing therapies previously defined as "long-term" pacing therapies.

20 Claims, 3 Drawing Sheets

SUPPRESSION OF HIGH RATE PACING FOR REDUCING MYOCARDIAL ISCHEMIC IRRITABILITY

FIELD OF THE INVENTION

The present invention relates generally to medical devices for delivering cardiac therapy to a patient, and in particular to a method and apparatus for controlling deliver of cardiac therapy in a medical device.

BACKGROUND OF THE INVENTION

Numerous pacing modalities exist which automatically adjust a cardiac pacing rate in response to sensor feedback. Typically a lower pacing rate is set at a minimum rate to maintain a base heart rate. Sensors that indicate a change metabolic need, such as activity sensors and minute ventilation sensors, are used in rate responsive pacemakers to adjust the pacing rate in response to a change in metabolic demand in closed-loop pacing rate control algorithms. A maximum upper rate is typically set as a nominal pacing rate that limits the sensor-indicated pacing rate.

Other examples of pacing modalities that can increase a pacing rate above a programmed lower rate include various tachycardia prevention pacing modalities, such as rate stabilization or rate smoothing pacing, atrial and ventricular overdrive pacing, post-mode switch overdrive pacing, and atrial preferred pacing. These various automatic rate-adjusting pacing therapies can result in relatively high rate pacing episodes. A high-rate pacing episode could induce or exacerbate myocardial ischemia, putting the patient at risk for myocardial injury or serious arrhythmias.

BRIEF SUMMARY OF THE INVENTION

The present invention relates to a medical device, such as an implantable cardiac stimulation device, capable of delivering automatic rate-adjusting pacing therapies having an adjustable upper rate limit responsive to an indication of myocardial irritability. The device, which may be embodied as a pacemaker, a pacemaker/cardioverter/defibrillator, or the like, is coupled to a set of electrodes for sensing cardiac electrogram (EGM) signals and delivering cardiac stimulation pulses. The device may be further coupled to or include other physiological sensors such as an activity sensor, minute ventilation sensor, pressure sensor, blood gas sensor, pH sensor or impedance sensors. The device uses the EGM signals and any other physiological sensors to monitor heart function and deliver cardiac stimulation therapies as appropriate.

In a method for controlling an upper pacing rate, the device detects an indicator of increased myocardial irritability. In one embodiment, an indicator of increased myocardial irritability is an arrhythmia episode. In particular, an episode of non-sustained or sustained ventricular tachycardia (VT) or ventricular fibrillation (VF) can be detected as an indicator of increased myocardial irritability. In another embodiment, an indicator of myocardial irritability is detection or prediction of a VT cluster or "storm" of either sustained or non-sustained ventricular tachyarrhythmia. In yet another embodiment, myocardial irritability is indicated by the presence of premature ventricular contractions (PVCs). A threshold requirement of a selected number of PVCs per minute can be defined as a determinant of irritability.

Upon detection of increased myocardial irritability, the upper rate limit for selected pacing therapies is adjusted to a predetermined rate lower than the programmed upper rate limit. In particular, the adjusted upper rate limit is applied to pacing therapies that are identified as long-term therapies. The upper rate limit applied to pacing therapies identified as short-term therapies remains at the programmed upper rate limit. The long-term pacing therapies and short-term pacing therapies are identified prospectively. In one embodiment long-term therapies are defined as therapies that typically result in sustained pacing delivery for eight or more cardiac cycles. Short-term therapies are defined as therapies that typically result in sustained pacing delivery for less than eight cardiac cycles.

The adjusted upper rate limit may be set to a predetermined nominal setting less than the programmed upper rate limit. The duration that the adjusted upper rate limit is applied to long-term pacing therapies may be set to a predetermined time interval. In some embodiments, the adjusted upper rate limit is selected based on patient heart rate and/or ischemia history. In other embodiments, methods for selecting an adjusted upper rate limit and the duration that it is in force use feedback from other physiological sensors or trended patient data.

An arrhythmia episode detected as an indicator of myocardial irritability can be combined with other ischemia detection methods for managing pacing therapies. In one embodiment, the detection of VT will cause another ischemia detection method to be invoked. The second ischemia detection method is used for selecting the adjusted upper rate limit or the duration for maintaining the adjusted upper rate limit.

DETAILED DESCRIPTION

Rate-responsive pacing and other pacing therapies aimed at maintaining a heart rate that is stable and meets the metabolic demands of the patient do not necessarily take into account the metabolic demand placed on the myocardium. A sensor-indicated rate for rate-responsive pacing or a pacing rate required to overcome an intrinsic rate during atrial preferred pacing, overdrive pacing or other self-adjusting pacing modes could pace the heart at a rate that produces demand-induced myocardial ischemia. To protect against ischemic injury or ischemia-induced arrhythmias, the maximum pacing rate that self-adjusting pacing modes are allowed to reach should be controlled in a way that reduces the likelihood of inducing or worsening an ischemic condition.

The invention is directed toward a method for controlling the maximum allowable pacing rate during self-adjusting pacing modes based on an indicator of cardiac insult, such as myocardial irritability, for example. "Myocardial irritability" as used herein refers to the condition where external stimulation is more likely to cause PVCs and contribute to proarrhythmic conditions by inducing or worsening ischemia and sympathetic activation. The occurrence of an arrhythmia is evidence of myocardial irritability and is often linked to myocardial ischemia. Thus, the present invention uses arrhythmia detection as a surrogate for ischemia detection for use in controlling an adjustable maximum pacing rate. In particular, to protect against ventricular ischemia or injury, VT episodes are detected as indicators of myocardial irritability for use in controlling an adjustable upper rate limit during rate-adjusting pacing therapies.

Figure 1:
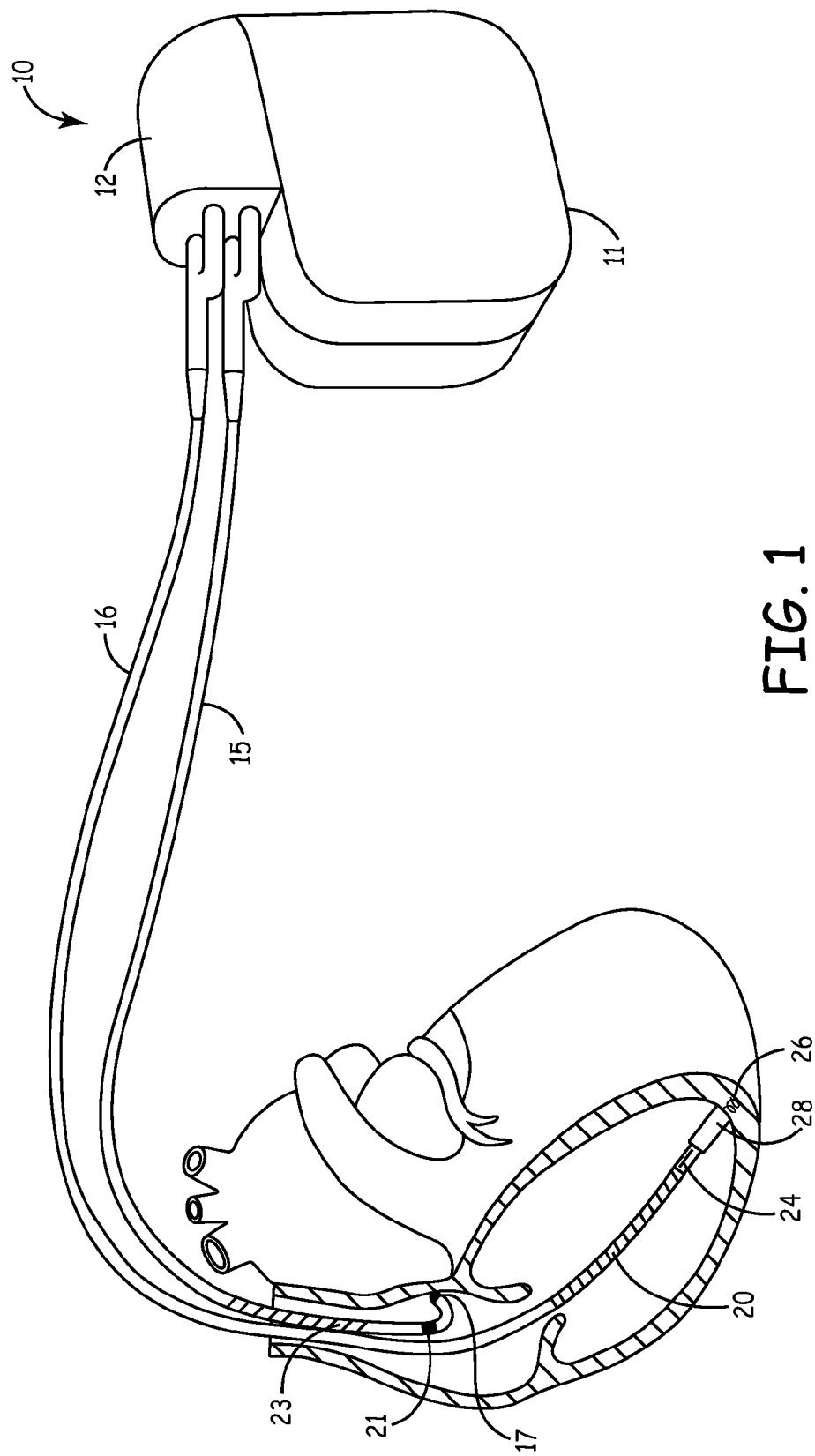
FIG. 1 is a schematic diagram of an exemplary medical device in which the present invention may be practiced.

FIG. 1 is a schematic diagram of an exemplary implantable cardiac stimulation device in which the present invention may be practiced. Device 10 is shown as an implantable cardioverter defibrillator (ICD) provided with dual-chamber pacemaking, cardioversion, and defibrillation capabilities. Such dual chamber devices sense both atrial and ventricular events for the detection of arrhythmias in both atrial and ventricular chambers. The present invention may be embodied in any single, dual or multichamber cardiac stimulation device that includes arrhythmia detection based on sensed EGM signals in one or more cardiac chambers. In particular, the present invention may be implemented within any cardiac stimulation device that includes EGM sensing for use in detecting ventricular tachycardia or fibrillation as an indicator of myocardial irritability.

To realize the benefits of the present invention, the cardiac stimulation device is capable of delivering rate-responsive pacing or other pacing therapies that include automatic pacing rate adjustment above a programmed lower rate in response to sensor feedback or a sensed heart rhythm. The cardiac stimulation device may provide various modes of pacing therapies such as dual chamber or multichamber pacing, cardiac resynchronization therapy, extra systolic stimulation, or arrhythmia prevention pacing therapies such as atrial preferred pacing, atrial or ventricular overdrive pacing, or rate smoothing or stabilization pacing. The device may also be capable of delivering anti-tachycardia pacing therapies such as high-frequency burst pacing. The device may further be capable of delivering higher voltage cardioversion/defibrillation pulses.

Device 10 is coupled to a patient's heart by way of a right atrial (RA) lead 15 and a right ventricular (RV) lead 16. A connector block 12 receives the proximal end of a right ventricular lead 16 and right atrial lead 15, used for positioning electrodes for sensing and stimulation. Right ventricular lead 16 is positioned such that its distal end is in the right ventricle for sensing right ventricular cardiac signals and delivering pacing or shocking pulses in the right ventricle. For these purposes, right ventricular lead 16 is equipped with a ring electrode 24, a tip electrode 26, optionally mounted retractably within an electrode head 28, and RV coil electrode 20, each of which are connected to an insulated conductor contained within the body of lead 16. The proximal end of the insulated conductors are coupled to corresponding connectors carried by a connector assembly at the proximal end of lead 16 for providing electrical connection to device 10.

The right atrial lead 15 is positioned such that its distal end is in the right atrium. Lead 15 is equipped with a ring electrode 21 and a tip electrode 17 for sensing and pacing in the right atrium. Lead 15 is further equipped with a superior vena cava (SVC) coil electrode 23 for delivering high-energy shock therapy. The ring electrode 21, the tip electrode 17 and the SVC coil electrode 23 are each connected to an insulated conductor within the body of the right atrial lead 15. Each insulated conductor is coupled at its proximal end to a connector carried by a connector assembly.

For pacing and sensing functions, the electrodes 17 and 21 or 24 and 26 may be used as bipolar pairs, commonly referred to as a "tip-to-ring" configuration, or individually in a unipolar configuration with the device housing 11 serving as the indifferent electrode, commonly referred to as the "can" or "case" electrode. The device housing 11 may also serve as a subcutaneous defibrillation electrode in combination with one or more of the defibrillation coil electrodes 20 or 23 for defibrillation of the atria or ventricles. It is recognized that alternate lead systems may be substituted for the lead system illustrated in FIG. 1. For example, the present invention may be practiced in implantable cardiac stimulation device systems involving pace/sense and cardioversion/defibrillation electrodes deployed intracardially, intravenously, epicardially, submuscularly, and/or subcutaneously.

Figure 2:
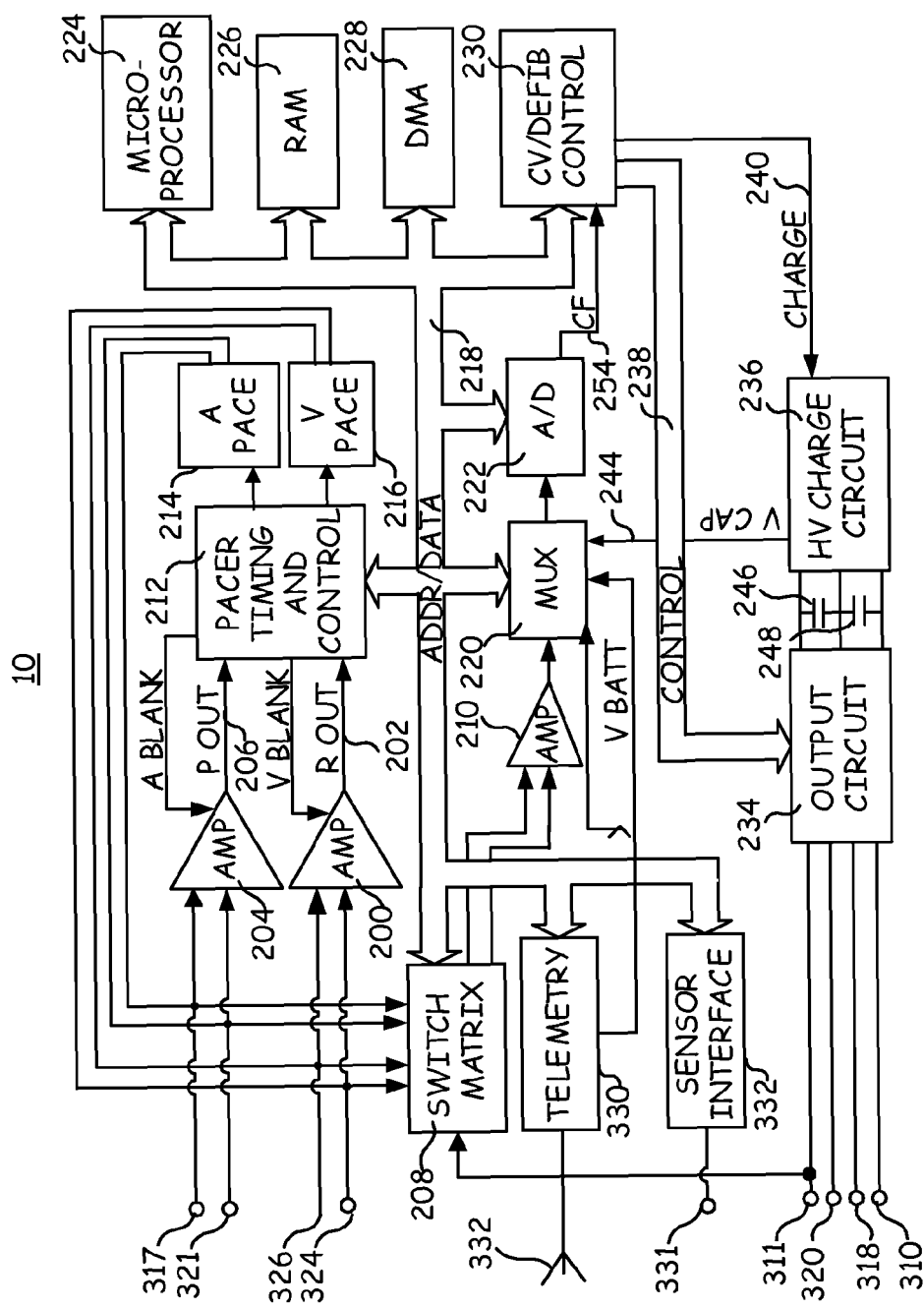
FIG. 2 is a functional block diagram of the device of FIG. 1.

FIG. 2 is a functional block diagram of the device of FIG. 1. This diagram should be taken as exemplary of the type of device with which the invention may be embodied and not as limiting, as it is believed that the invention may usefully be practiced in a wide variety of device implementations. For example, the disclosed embodiment shown in FIG. 2 is a microprocessor-controlled device, but the methods of the present invention may also be practiced with devices employing dedicated integrated circuitry for controlling device functions.

With regard to the electrode system illustrated in FIG. 1, device 10 is provided with a number of connection terminals for achieving electrical connection to the cardiac leads 15 and 16 and their respective electrodes. The connection terminal 311 provides electrical connection to the housing 11 for use as the indifferent electrode during unipolar stimulation or sensing. The connection terminals 310 and 320 provide electrical connection to coil electrodes 20 and 23. Each of these connection terminals 311, 310, and 320, are coupled to the high voltage output circuit 234 to facilitate the delivery of high energy shocking pulses to the heart using one or both of the coil electrodes 20 and 23 and optionally the housing 11.

The connection terminals 317 and 321 provide electrical connection to tip electrode 17 and ring electrode 21 positioned in the right atrium. The connection terminals 317 and 321 are further coupled to an atrial sense amplifier 204 for sensing atrial signals such as P-waves. The connection terminals 326 and 324 provide electrical connection to tip electrode 26 and the ring electrode 24 positioned in the right ventricle. The connection terminals 326 and 324 are further coupled to a ventricular sense amplifier 200 for sensing ventricular signals.

The atrial sense amplifier 204 and the ventricular sense amplifier 200 preferably take the form of automatic gain controlled amplifiers with adjustable sensing thresholds. The general operation of the ventricular sense amplifier 200 and the atrial sense amplifier 204 may correspond to that disclosed in U.S. Pat. No. 5,117,824, by Keimel, et al. Whenever a signal received by atrial sense amplifier 204 exceeds an atrial sensing threshold, a signal is generated on the P-out signal line 206. Whenever a signal received by the ventricular sense amplifier 200 exceeds a ventricular sensing threshold, a signal is generated on the R-out signal line 202.

Switch matrix 208 is used to select which of the available electrodes are coupled to a wide band amplifier 210 for use in digital signal analysis. Selection of the electrodes is controlled by the microprocessor 224 via data/address bus 218. The selected electrode configuration may be varied as desired for the various sensing, pacing, cardioversion and defibrillation functions of the device 10. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm based on EGM information employing any of the numerous signal processing methods known in the art. EGM signal information is employed for detecting atrial and ventricular rates for the purposes of the present invention, however, it is recognized that alternative signals, such as mechanical signals, may be used for deriving cardiac rates and may be used in conjunction with the present invention in addition to or in place of electrical signals.

In some embodiments of the present invention, device 10 includes ischemia monitoring based on EGM signal analysis. EGM signals passed to amplifier 210 may be analyzed by microprocessor 224 to detect changes indicative of myocardial ischemia. For example, ischemia detection based on variation in the ST segment of the EGM signal is generally described in U.S. Pat. No. 6,128,526 issued to Stadler, et al., incorporated herein by reference in its entirety.

Device 10 may further include or be coupled to other physiological sensors for use in monitoring heart function or metabolic need of the patient. A sensor 331 coupled to a sensor interface 332 is included in some embodiments of device 10 for providing a sensor-indicated pacing rate. Sensor 331 may be implemented as an activity sensor, a minute ventilation sensor or other sensor responsive to changes in systemic metabolic demand. Sensor signals are passed via address/data bus 218 to microprocessor 224 for use in determining an appropriate pacing rate to meet the metabolic demands of the patient. Methods and circuitry for providing rate responsive pacing according to a sensor-indicated rate are known in the art.

The telemetry circuit 330 receives downlink telemetry from and sends uplink telemetry to an external programmer, as is conventional in implantable cardiac stimulation devices, by means of an antenna 332. Received telemetry is provided to microprocessor 224 via multiplexer 220. Data to be uplinked to the programmer and control signals for the telemetry circuit 330 are provided by microprocessor 224 via address/data bus 218. Data to be uplinked may include a record of detected and classified arrhythmia episodes as is customary in modern ICDs. Numerous types of telemetry systems known for use in implantable devices may be used.

The remainder of circuitry illustrated in FIG. 2 is dedicated to the provision of cardiac pacing, cardioversion and defibrillation therapies. In the exemplary embodiment shown in FIG. 2, the pacer timing and control circuitry 212 includes programmable digital counters which control the basic time intervals associated with various pacing modes delivered in the atria or ventricles. Pacer circuitry 212 also determines the amplitude of the cardiac pacing pulses under the control of microprocessor 224.

During pacing, escape interval counters within pacer timing and control circuitry 212 are reset upon sensing of R-waves or P-waves as indicated by signals on lines 202 and 206, respectively. In accordance with the selected mode of pacing, pacing pulses are generated by atrial pacer output circuit 214 and ventricular pacer output circuit 216. The pacer output circuits 214 and 216 may be coupled to the desired electrodes for pacing via switch matrix 208. The escape interval counters are reset upon generation of pacing pulses, and thereby control the basic timing of cardiac pacing functions, including tachycardia prevention pacing and anti-tachycardia pacing.

The durations of the escape intervals are determined by microprocessor 224 via data/address bus 218. The value of the count present in the escape interval counters when reset by sensed R-waves or P-waves can be used to measure R-R intervals, P-P intervals, P-R intervals, and R-P intervals, which measures are stored in memory 226 and for use in diagnosing the occurrence of a variety of arrhythmias.

A variety of pacing therapies may be available including bradycardia pacing, rate-responsive pacing, anti-tachycardia pacing, cardiac resynchronization pacing, extra-systolic stimulation, rate smoothing or stabilization pacing, overdrive pacing, and atrial preference pacing, or other tachyarrhythmia prevention pacing modes. Examples of various tachyarrhythmia prevention pacing modes are generally described in U.S. Pat. No. 6,442,429 issued to Hill et al., U.S. Pat. No. 5,978,709 issued to Begemann et al., U.S. Pat. No. 4,941,471 issued to Mehra, U.S. Pat. No. RE37480 issued to Denker, U.S. Pat. No. 5,814,085 issued to Hill, U.S. Pat. No. 5,713,929 issued to Hess, et al., and U.S. Pat. No. 6,185,459 issued to Mehra, et al.

Control algorithms for setting the pacing rate during rate responsive pacing, overdrive pacing, atrial prevention pacing and other pacing modes will automatically adjust the pacing rate as appropriate within the bounds of a programmed lower rate and a programmed upper rate limit. The programmed lower rate and the programmed upper rate limits define the lower and upper heart rates considered to be safe for the particular patient. In past practice, these upper and lower rate limits are commonly set to nominal values and do not change with changing patient condition.

In accordance with the present invention, the various pacing therapies provided by the device will be divided into classifications of "short-term" therapies and "long-term" therapies. The invention provides adjustment of the upper rate limit during the delivery of long-term pacing therapies in response to a detection of myocardial irritability while retaining the unaltered function of short-term therapies. Generally, "long-term" therapies refer to therapies that typically result in a sustained pacing episode of longer than about 8 to 10 cardiac cycles and will exclude anti-tachycardia pacing therapies. "Long-term" therapies may alternatively be defined as therapies that will potentially result in sustained pacing episodes of greater than a predetermined interval of time, such as greater than about 10 seconds. The classification of therapies as "long-term" and "short-term" therapies may vary between embodiments and may be based on clinician preference or patient history and ischemia risk. Examples of therapies that will typically be classified as "long-term" therapies include rate-responsive pacing, atrial preference pacing, atrial or ventricular overdrive pacing, and post-mode switch overdrive pacing. In some implementations, ventricular tracking of an atrial rate may be classified as a "long-term" therapy and subjected to upper rate limit adjustment. Ventricular tracking of the atrial rate may be applied via pseudo-Wenckebach timing rules as known in the art. In other embodiments, ventricular tracking of an atrial rate may be not be subjected to an adjusted upper rate limit to allow an intrinsic atrial rate to guide the ventricular rate.

Examples of therapies that will typically be classified as "short-term" therapies include ventricular and atrial rate stabilization pacing and any anti-tachycardia pacing. An adjusted upper rate limit is not applied to short-term pacing therapies. Pacing at a high rate for a short term is assumed to have insignificant effects on myocardial ischemia. The benefit of the short-term pacing therapy likely outweighs any associated risk of inducing or exacerbating myocardial ischemia.

Microprocessor 224 operates as an interrupt driven device and is responsive to interrupts from pacer timing and control circuitry 212 corresponding to the occurrences of sensed P-waves and R-waves and corresponding to the generation of cardiac pacing pulses. Any necessary mathematical calculations to be performed by microprocessor 224 and any updating of the values or intervals controlled by pacer timing/ control circuitry 212 take place following such interrupts. A portion of the random access memory 226 may be configured as a number of recirculating buffers capable of holding a series of measured intervals, which may be analyzed in response to a pace or sense interrupt by microprocessor 224 for diagnosing an arrhythmia. Any of the various arrhythmia detection methodologies known in the art may be employed in conjunction with the present invention for detecting and classifying arrhythmias.

In response to the detection of atrial flutter or ventricular tachycardia, an anti-tachycardia pacing therapy may be delivered if desired by loading a regimen from microcontroller 224 into the pacer timing and control circuitry 212 according to the type of tachycardia detected. In the event that higher voltage cardioversion or defibrillation shock pulses are required, microprocessor 224 activates the cardioversion and defibrillation control circuitry 230 to initiate charging of the high voltage capacitors 246 and 248 via charging circuit 236 under the control of high voltage charging control line 240. The voltage on the high voltage capacitors 246 and 248 is monitored via a voltage capacitor (VCAP) line 244, which is passed through the multiplexer 220. When the voltage reaches a predetermined value set by microprocessor 224, a logic signal is generated on the capacitor full (CF) line 254, terminating charging. Thereafter, timing of the delivery of the defibrillation or cardioversion pulse is controlled by pacer timing and control circuitry 212.

In the illustrated device, delivery of cardioversion or defibrillation pulses is accomplished by output circuit 234, under control of control circuitry 230 via control bus 238. Output circuit 234 determines the shock pulse waveform, e.g. whether a monophasic, biphasic or multiphasic pulse is delivered, whether the housing 311 serves as cathode or anode, which electrodes are involved in delivery of the pulse, and the pulse shape and tilt.

In modern implantable cardioverter defibrillators, the particular therapies are programmed into the device ahead of time by the physician, and a menu of therapies is typically provided. For example, on initial detection of tachycardia, an anti-tachycardia pacing (ATP) therapy may be selected. On redetection of tachycardia, a more aggressive ATP therapy may be scheduled. If repeated attempts at ATP therapies fail, a higher-level cardioversion pulse therapy may be selected thereafter. The amplitude of the defibrillation shock may be incremented in response to failure of an initial shock or shocks to terminate fibrillation.

Figure 3:
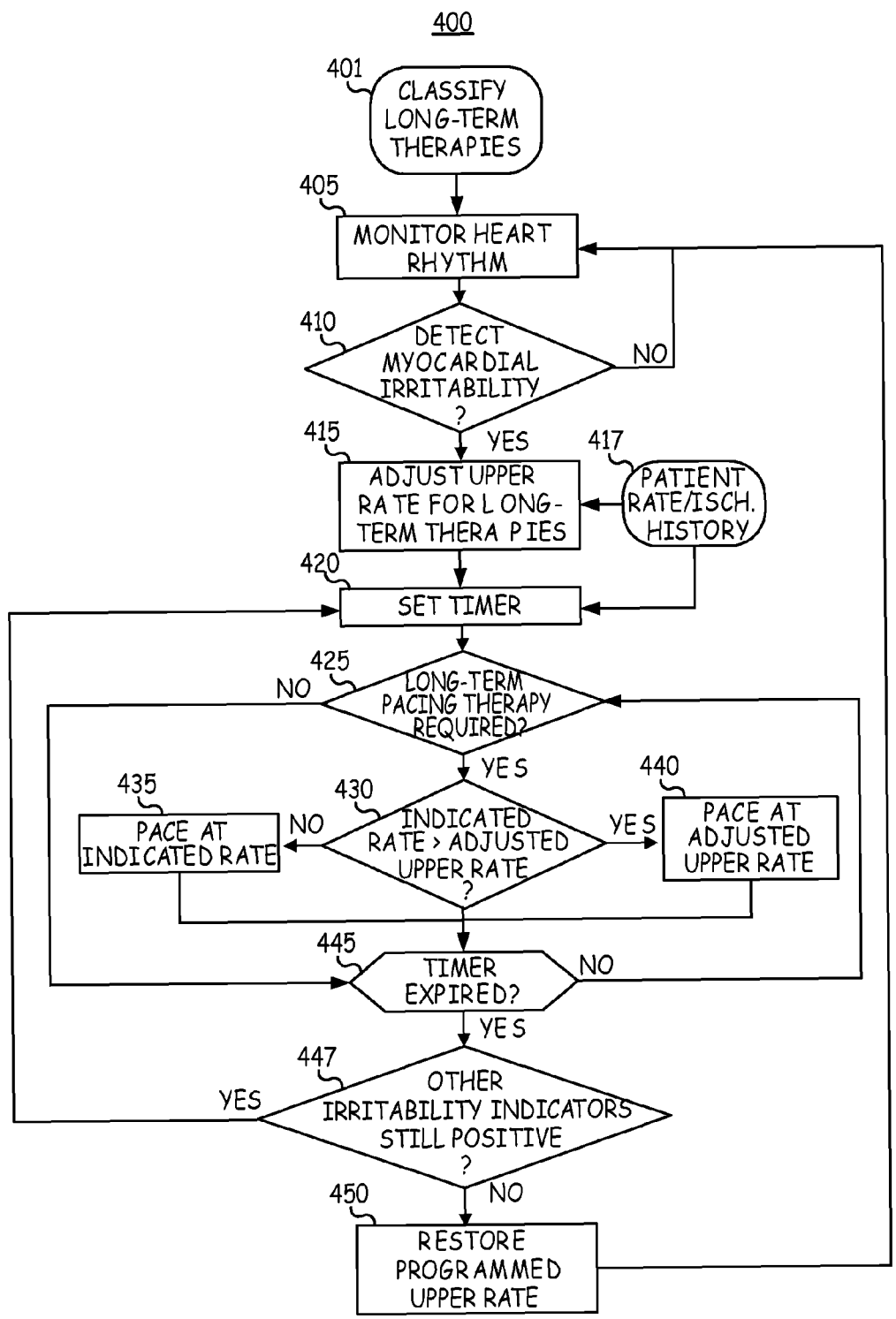
FIG. 3 is a flow chart of a method for adjusting an upper rate limit in response to detecting an indicator of myocardial irritability according to an embodiment of the present invention.

FIG. 3 is a flow chart summarizing a method for adjusting an upper rate limit in response to detecting an indicator of myocardial irritability. At step 401, pacing therapies provided by the device in which method 400 is being implemented are classified as "long-term" or "short-term" therapies. Therapies classified as "long-term" therapies are those that will be restricted by an adjusted upper rate limit. Therapies classified as "short-term" therapies are those that will be restricted by the programmed upper rate limit and not affected by an adjusted upper rate limit. Pacing therapies that are generally classified as "long-term" are those typically expected to result in pacing episodes lasting for more than about 8 to 10 cardiac cycles. Examples of pacing therapies that may be classified as "long-term" include rate responsive pacing, atrial preferred pacing, atrial or ventricular overdrive pacing, and post-mode switch overdrive pacing. Other pacing therapies that are typically short-term interventions lasting for only several cardiac cycles are not limited by the adjusted upper rate limit. Examples of short-term pacing interventions may include atrial or ventricular rate stabilization pacing and any anti-tachycardia pacing therapies.

At step 405, the heart rhythm is monitored by sensing and analyzing EGM signals. Detected arrhythmia episodes are interpreted as an indicator of myocardial irritability. In one embodiment, if an episode of ventricular tachycardia (VT) or ventricular fibrillation (VF) is detected, myocardial irritability is detected at decision step 410. The detected episode may be a sustained episode, requiring anti-arrhythmia therapy delivery, or a non-sustained episode that spontaneously reverts to normal sinus rhythm.

In other embodiments, myocardial irritability is detected at step 410 when recurrent VT episodes, sometimes referred to as a VT cluster or VT storm, are detected or predicted. Prediction of a VT cluster or VT storm may be performed according to methods generally disclosed in U.S. Pat. No. 6,922, 585, filed Apr. 14, 2002, entitled "Method and Apparatus for Predicting Recurring Ventricular Arrhythmias", to Zhou et al., incorporated herein by reference in its entirety.

In still other embodiments, other criteria relating to PVCs are defined as indicators of myocardial irritability. For example, detection of a minimum rate of PVCs may be set as myocardial irritability detection criteria. In one implementation, if PVCs are detected at a rate of at least 10 PVCs per minute, myocardial irritability is detected. PVC detection may be implemented according to methods known in the art. Typically PVC detection is based on R-wave detection without an associated P-wave detection prior to the R-wave detection (two consecutive R-wave detections without an intervening P-wave).

If myocardial irritability is detected at step 410 based on detection or prediction of a VT or VF episode or other irritability indicator, the upper rate limit for long-term therapies is adjusted at step 415. The upper rate limit is reduced to a rate lower than a programmed upper rate limit. The adjusted upper rate limit may be set to a nominal value, set to a percentage of the programmed upper rate limit or to a predetermined amount less than the programmed upper rate limit.

Alternatively, patient heart rate and/or ischemia history may be used in selecting an adjusted upper rate limit as indicated by data input step 417. In one embodiment, the adjusted upper rate limit is based on historical data relating heart rate to measured ischemia. Methods known in the art for monitoring ischemia using EGM signals, such as S-T segment elevation, may be used for obtaining rate-ischemia data automatically. Rate-ischemia data stored by the implantable device can be used in a closed-loop fashion for selecting the upper rate limit to a rate below rates associated with ischemia detection. Rate-ischemia data may alternatively be obtained during clinical stress testing, and the adjusted upper rate limit may be programmed by a clinician based on clinical data.

In another embodiment, the adjusted upper rate limit is based on historical intrinsic heart rate data. The identification of uncommon rates, e.g., an upper percentile of heart rates that occur over a relatively long period of monitoring, such as a week, month or year, may be used in setting an adjusted upper rate limit. The adjusted upper rate limit may be set at a rate below an identified uncommon rate. Uncommon rates may be identified by an algorithm implemented in the implantable device using stored heart rate data or by a clinician using data uplinked from an implantable device or clinical monitoring data.

The adjusted upper rate limit is applied to any pacing therapy that has been classified or selected as a "long-term" therapy. At step 420, a timer is set for a time interval during which the adjusted upper rate limit will be in effect for limiting the maximum pacing rate during any long-term pacing therapy delivery. The time interval may be set to a predetermined nominal duration, for example a period for 4 hours, 8 hours, 24 hours, or otherwise. In other embodiments, the time interval may be set based on historical patient heart rate and/or ischemia data as indicated by data input block 417. Data stored by the implanted device may be used to derive rate-related or arrhythmia-related ischemia episode durations used in selecting the adjusted upper rate limit duration. In another embodiment, the history of post-exercise baseline rate recovery is used in selecting an adjusted upper rate limit duration. In one example, the fastest historical rate associated with a selected rate deceleration threshold upon discontinuation of activity or exercise is used as the adjusted upper rate limit. For example, in a 9-month history of the device, the fastest measure rate associated with a rate deceleration of at least 18 bpm/minute is used as the adjusted upper rate limit.

After setting a timer to an appropriate duration at step 420, the ICD determines if a pacing therapy that has been classified as "long-term" is required at decision step 425. If any long-term pacing therapies are invoked, the indicated pacing rate is compared to the adjusted upper rate limit at decision step 430. The indicated pacing rate may be a sensor-indicated rate (as in rate-responsive pacing) or a rate selected based on an underlying intrinsic rate (as in atrial preference pacing or overdrive pacing). Any time the indicated pacing rate exceeds the adjusted upper rate limit, pacing pulses are delivered at the adjusted upper rate at step 440. As long as the indicated rate remains below the adjusted upper rate, pacing occurs at the indicated rate at step 435. As noted previously, any need for short-term pacing therapies is responded to without adjustment of the upper rate limit. Pacing at the programmed upper rate limit for a few cardiac cycles is assumed to have insignificant effects on myocardial ischemia such that the benefit of the short-term pacing therapy outweighs any associated risk of inducing or exacerbating myocardial ischemia.

Upon expiration of the timer at step 445, the programmed upper rate limit is restored at step 450. Any "long-term" pacing therapies in process or invoked after timer expiration may deliver pacing pulses at any rate up to the programmed upper rate limit. Method 400 returns to step 405 to continue monitoring the heart rhythm and detecting myocardial irritability based on arrhythmia episode detections.

Alternatively, other irritability indicators may be monitored at decision step 447 and taken into account prior to restoring a programmed upper rate limit. Other irritability indicators that may be monitored include a recurrence of a VT or VF during the applied adjusted upper rate limit interval, the frequency of premature contractions, ischemia detection, or a change in a monitored hemodynamic or other cardiac function parameter such as blood pressure or wall motion. If other indicators are positive for myocardial irritability or a sustained risk of ischemia, method 400 returns to step 420 and resets the timer to extend the duration of adjusted upper rate limit. The timer may be reset to the same interval as previously set at step 420 or to a different, shorter or longer, interval based on the other irritability indicators identified at step 447.

Thus, a system and method have been described which provide an adjustable upper rate limit responsive to detection of an arrhythmia episode as an indicator of myocardial irritability. Aspects of the present invention have been illustrated by the exemplary embodiments described herein. Numerous variations to these embodiments may be conceived by one having skill in the art and the benefit of the teachings provided herein. The described embodiments are intended to be illustrative of methods for practicing the invention and, therefore, should not be considered limiting with regard to the following claims.

What is claimed is:

1. A method of controlling delivery of therapy in a medical device, comprising:
   sensing physiologic signals of a patient;
   delivering the therapy in response to the sensed signals;
   determining the presence of increased myocardial irritability that occurs in response to the delivered therapy; and
   adjusting an upper pacing rate limit associated with the delivering of the therapy to an adjusted upper pacing rate limit below a programmed upper pacing rate limit in response to determining the presence of increased myocardial irritability occurring in response to the delivered therapy, wherein determining the presence of increased myocardial irritability comprises detecting one of a non-sustained ventricular tachycardia event that spontaneously reverts to normal sinus rhythm, a non-sustained ventricular fibrillation event that spontaneously reverts to normal sinus rhythm, a minimum rate of premature ventricular contractions, and prediction of a ventricular tachycardia cluster.

2. The method of claim 1, further comprising:
   determining whether a current pacing rate is greater than the adjusted upper pacing rate limit; and
   delivering the therapy at the adjusted upper pacing rate limit in response to the current pacing rate being greater than the adjusted upper pacing rate limit.

3. The method of claim 1, further comprising:
   determining whether a predetermined time period associated with the adjusted upper pacing rate limit has expired; and
   adjusting the upper pacing rate limit from the adjusted upper pacing rate limit to the programmed upper pacing rate limit in response to determining that the predetermined time period has expired.

4. The method of claim 3, further comprising:
   monitoring physiologic data of the patient; and
   adjusting the predetermined time period in response to the monitored physiologic data.

5. The method of claim 1, further comprising monitoring physiologic data of the patient, wherein the adjusted upper pacing rate limit corresponds to the monitored physiologic data.

6. The method of claim 1, further comprising:
   determining whether a predetermined time period associated with the adjusted upper pacing rate limit has expired;
   determining the presence of increased myocardial irritability that occurs in response to the delivering of the therapy at the adjusted upper pacing rate limit; and
   adjusting the upper pacing rate limit from the adjusted upper pacing rate limit to the programmed upper pacing rate limit in response to determining that the predetermined time period has expired and determining no increased myocardial irritability being present in response to the delivering of the therapy at the adjusted upper pacing rate limit.

7. The method of claim 1, further comprising;
   determining whether a predetermined time period associated with the adjusted upper pacing rate limit has expired;
   determining, in response to determining that the predetermined time period has expired, the presence of increased myocardial irritability that occurs in response to the delivering of the therapy at the adjusted upper pacing rate limit;
   adjusting the upper pacing rate limit from the adjusted upper pacing rate limit to the programmed upper pacing rate limit in response to determining no increased myocardial irritability being present in response to the delivering of the therapy at the adjusted upper pacing rate limit; and adjusting the predetermined time period in response to determining increased myocardial irritability is present in response to the delivering of the therapy at the adjusted upper pacing rate limit.

8. The method of claim 7, further comprising monitoring physiologic data of the patient, wherein the predetermined time period is adjusted in response to the monitored physiologic data.

9. The method of claim 1, wherein adjusting the upper pacing rate limit comprises:

determining whether the therapy is one of a short term therapy having a first duration or a long term therapy having a second duration greater than the first duration; and adjusting the upper pacing rate limit in response to determining the presence of increased myocardial irritability occurring in response to the delivered therapy and determining that the therapy is a long term therapy.

10. A medical device for delivering therapy to a patient, comprising:

a plurality of electrodes configured to sense physiologic signals of a patient and deliver the therapy;

a control unit, coupled to the plurality of electrodes, configured to control delivery of the therapy in response to the sensed signals;

a microprocessor, coupled to the control unit, configured to determine the presence of increased myocardial irritability that occurs in response to the delivered therapy, wherein the control unit is further configured to adjust an upper pacing rate limit associated with the delivery of the therapy to an adjusted upper pacing rate limit below a programmed upper pacing rate limit in response to the microprocessor determining the presence of increased myocardial irritability that occurs in response to the delivered therapy, wherein determining the presence of increased myocardial irritability comprises detecting one of a non-sustained ventricular tachycardia event that spontaneously reverts to normal sinus rhythm, a non-sustained ventricular fibrillation event that spontaneously reverts to normal sinus rhythm, a minimum rate of premature ventricular contractions, and prediction of a ventricular tachycardia cluster.

11. The device of claim 10, wherein the control unit is configured to control the delivery of the therapy at the adjusted upper pacing rate limit in response to a current pacing rate being greater than the adjusted upper pacing rate limit.

12. The device of claim 10, wherein the microprocessor determines whether a predetermined time period associated with the adjusted upper pacing rate limit has expired, and the control unit adjusts the upper pacing rate limit from the adjusted upper pacing rate limit to the programmed upper pacing rate limit in response to determining that the predetermined time period has expired.

13. The device of claim 12, wherein the microprocessor monitors physiologic data of the patient, and the control unit adjusts the predetermined time period in response to the monitored physiologic data.

14. The device of claim 10, wherein the microprocessor monitors physiologic data of the patient, wherein the adjusted upper pacing rate limit corresponds to the monitored physiologic data.

15. The device of claim 10, wherein the microprocessor determines whether a predetermined time period associated with the adjusted upper pacing rate limit has expired and determines the presence of increased myocardial irritability that occurs in response to the delivery of the therapy at the adjusted upper pacing rate limit, and wherein the control unit adjusts the upper pacing rate limit from the adjusted upper pacing rate limit to the programmed upper pacing rate limit in response to the predetermined time period having expired and no increased myocardial irritability being present in response to the delivering of the therapy at the adjusted upper pacing rate limit.

16. The device of claim 10, wherein the microprocessor determines whether a predetermined time period associated with the adjusted upper pacing rate limit has expired and determines, in response to determining that the predetermined time period has expired, the presence of increased myocardial irritability that occurs in response to the delivery of the therapy at the adjusted upper pacing rate limit, and wherein the control unit adjusts the upper pacing rate limit from the adjusted upper pacing rate limit to the programmed upper pacing rate limit in response to no increased myocardial irritability being present in response to the delivering of the therapy at the adjusted upper pacing rate limit, and adjusts the predetermined time period in response to increased myocardial irritability occurring in response to the delivery of the therapy at the adjusted upper pacing rate limit.

17. The device of claim 16, wherein the microprocessor monitors physiologic data of the patient, and wherein the predetermined time period is adjusted in response to the monitored physiologic data.

18. The medical device of claim 10, wherein the microprocessor determines whether the delivered therapy is one of a short term therapy having a first duration and or a long term therapy having a second duration greater than the first duration, and wherein the control unit adjusts the upper pacing rate limit in response to the microprocessor determining the presence of increased myocardial irritability that occurs in response to the delivered therapy and determining that the therapy is a long term therapy.

19. A method of controlling delivery of therapy in a medical device, comprising:

sensing physiologic signals of a patient;

determining the presence of a cardiac event in response to the sensed signals;

delivering the therapy at a predetermined pacing rate in response to the determined cardiac event;

determining whether the delivered therapy is one of a short term therapy having a first duration and a long term therapy having a second duration greater than the first duration;

continuing delivery of the therapy at the predetermined pacing rate in response to the delivered therapy being a short term therapy;

determining, in response to the delivered therapy being a long term therapy, whether an increase in myocardial irritability occurs in response to the delivered therapy; and reducing an upper pacing rate limit associated with the delivering of the therapy to an adjusted upper pacing rate limit below a programmed upper rate limit in response to an increase myocardial irritability occurring in response to the delivered therapy, wherein determining whether an increase in myocardial irritability occurs comprises detecting one of a non-sustained ventricular tachycardia event that spontaneously reverts to normal sinus rhythm, a non-sustained ventricular fibrillation event that spontaneously reverts to normal sinus rhythm, a minimum rate of premature ventricular contractions, and prediction of a ventricular tachycardia cluster.

20. The method of claim 19, further comprising:
determining, during delivery of the therapy utilizing the adjusted upper pacing rate limit, an indicated pacing rate, the indicated pacing rate corresponding to one of a sensor-indicated pacing rate and an intrinsic pacing rate;
determining whether the indicated pacing rate is greater than the adjusted upper pacing rate limit;
delivering the therapy at the indicated pacing rate in response to the indicated pacing rate not being greater than the adjusted upper pacing rate limit; and
delivering the therapy at the adjusted upper pacing rate limit in response to the indicated pacing rate being greater than the adjusted upper pacing rate limit.

* * * * *